US00PP16478P3

(12) United States Plant Patent
Luby et al.

(10) Patent No.: US PP16,478 P3
(45) Date of Patent: Apr. 25, 2006

(54) GRAPE PLANT NAMED 'FRONTENAC GRIS'

(50) Latin Name: ***Vitis* spp hybrid**
Varietal Denomination: Frontenac gris

(75) Inventors: James Luby, St. Paul, MN (US); Peter Hemstad, Edina, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 214 days.

(21) Appl. No.: 10/775,435

(22) Filed: Feb. 10, 2004

(65) Prior Publication Data

US 2004/0237158 P1 Nov. 25, 2004

Related U.S. Application Data

(60) Provisional application No. 60/446,660, filed on Feb. 11, 2003.

(51) Int. Cl.
*A01H 5/00* (2006.01)

(52) U.S. Cl. ..... Plt./205
(58) Field of Classification Search ..... Plt./205
See application file for complete search history.

*Primary Examiner*—Anne Marie Grunberg
(74) *Attorney, Agent, or Firm*—Penny J. Aguirre

(57) ABSTRACT

The invention is a new and distinct variety of grape plant designated 'Frontenac gris', which produces gray colored fruit suitable for white wine production, and has a combination of high wine quality, excellent cold hardiness and disease resistance, and very good productivity.

4 Drawing Sheets

Botanical classification: *Vitis* spp hybrid.
Variety denomination: 'Frontenac gris'.

BACKGROUND OF THE INVENTION

Most grape varieties used for production of high quality wines around the world are of the species *Vitis vinifera*. These *V. vinifera* varieties, when cultivated in northern regions of the United States with a continental climate, are often subject to serious injury or death from low temperatures during winter. Although several wild *Vitis* species occur in colder regions of North America and eastern Asia, the wine made from these species generally has serious defects. Thus, there is a need for grape varieties that are winter hardy, yet produce fruit capable of yielding high quality wine. A grape breeding program at the University of Minnesota has been engaged in developing such varieties since the early 1980s.

BRIEF SUMMARY OF THE INVENTION

'Frontenac gris' is a variety of grape (*Vitis* hybrid) with gray (or gris, in French) colored fruit suitable for white wine production, and is well adapted to the Upper Midwest climate of the United States. 'Frontenac gris' has an unusual combination of high wine quality, excellent cold hardiness and disease resistance, and very good productivity. 'Frontenac gris' was originally identified as a sport of 'Frontenac' (unpatented), a variety of grape of hybrid origin with bluish black colored fruit with red juice suitable for red wine production that was introduced in 1996 by the grape breeding program at the University of Minnesota Horticultural Research Center (HRC) in Carver County, Minn.

'Frontenac gris' propagates readily from hardwood cuttings, with young vines quick to become established, and all 'Frontenac gris' plants propagated in this manner have been genetically stable, producing only gray colored fruit with clear juice. As grown in east central Minnesota, the plants of 'Frontenac gris' are vigorous, productive, and winter hardy. The vines of 'Frontenac gris' have relatively few tendrils and an open growth habit well suited to upper cordon training systems. The budbreak and bloom of 'Frontenac gris' are early to midseason, and its flowers are perfect and self-fertile. 'Frontenac gris' vines typically set a moderate to heavy crop. The fruit of 'Frontenac gris' is borne on medium sized clusters that are usually somewhat loose, and the berries are small and gray with a waxy bloom at maturity. Berry splitting and bunch rots have rarely been observed, even under wet conditions in the autumn harvest season. In some years, over-cropping may occur and cluster thinning may be required. In east central Minnesota, the fruit typically ripens around September 29, about three days after fruit of the 'Seyval' variety (unpatented), and at harvest is usually relatively high in both sugar and acidity. When grown in Minnesota, the fruit of 'Frontenac gris' has a high titratable acidity which usually requires either malolactic fermentation or residual sugar in order to produce a well balanced wine, and when grown in regions experiencing greater degree day accumulations, the acidity has been substantially lower.

The fruit of 'Frontenac gris' can be fermented to produce either white table wine or dessert wine, and such wines have been well received in various tastings. The wine tends to have good body and pleasant aromas, with very little of the herbaceous qualities associated with *V. riparia* and many interspecific grape hybrids. 'Foxy aromas' derived from *V. labrusca* have not been detected. The most common aroma component identified by tasters has been peach, but apricot, citrus, and tropical fruit aromas have also been noted. At times the wine may exhibit a slightly pink or peach coloration derived from the lightly pigmented skin of the fruit.

'Frontenac gris', like 'Frontenac', has exhibited resistance to several important diseases in evaluations. Even under conditions of high disease pressure, 'Frontenac gris' is highly resistant to downy mildew (*Plasmopara viticola*) on both the foliage and the fruit. 'Frontenac gris' is moderately resistant to powdery mildew (*Uncinula necator*), which has been observed frequently at low levels on the foliage, but has not been seen on the fruit. 'Frontenac gris' is moderately resistant to black rot (*Guignardia bidwellii*), which has been observed sporadically and at low levels on the foliage and the fruit. Anthracnose (*Elsinoe ampelina*) has rarely been observed on the foliage and fruit of 'Frontenac gris'. 'Frontenac gris' is susceptible to the foliar form of grape phylloxera (*Daktulosphaira vitifoliae*) while tolerant to the root form of this disease. 'Frontenac gris' is tolerant to the adverse effects of phenoxy herbicide drift.

'Frontenac gris' has proven to be sufficiently cold hardy for consistent production in east central Minnesota where temperatures frequently reach −35° C. during the winter season. Field tests have shown 'Frontenac gris' to be at least as cold hardy as the 'Marachal Foch' variety (unpatented), and substantially cold hardier than the 'Seyval' variety and most other presently available grape cultivars used for wine production.

BRIEF DESCRIPTION OF THE FIGURES

The accompanying color photographs were taken in mid September and represent typical mature berry clusters and vines of 'Frontenac gris' and 'Frontenac' as grown under standard field conditions in Excelsior, Minn.

The Photograph in FIG. 1 is a close-up view of clusters of berries of 'Frontenac gris'.

The photographs in FIG. 1 and FIG. 3 provide a comparison between the berry clusters of 'Frontenac gris' (FIG. 2) and 'Frontenac' (FIG. 3).

FIG. 4 and FIG. 5 are photographs comparing mature vines of 'Frontenac gris' and 'Frontenac', respectively.

FIG. 6 is a drawing taken from Dettweiler E., 1991, 'Preliminary Minimal Descriptor List for Grapevine Varieties', Institüt fur Rebenzüchtung, Geilweilerhof, Germany: N1 is the length along the primary vein (midrib) from the tip of the blade to the petiole sinus, N2 is the length of the vein from the tip of the first major lobe of the blade to the petiole sinus, N3 is the length of the vein from the tip of the second major lobe of the blade to the petiole sinus, N4 is the length of the vein from the tip of the third major lobe of the blade to where it joins the vein measured in N3, N5 in the length of the vein from the tip of the first tooth proximal to the petiole sinus to where it joins the vein measured in N4.

The colors in the photographs are as close as possible with the photographic and printing technology utilized. The color values cited in the detailed botanical description accurately describe the colors of the new grape.

DETAILED BOTANICAL DESCRIPTION

'Frontenac gris' arose from the spontaneous mutation of the 'Frontenac' variety in 1992. 'Frontenac' arose from a controlled cross as part of the grape breeding program at the University of Minnesota Horticultural Research Center (HRC) in Carver County, Minn., and originated from the cross designated GE 7828 and made in 1978 between the French hybrid variety 'Landot 4511' (unpatented) and the University of Minnesota *Vitis riparia* clone #89 found growing wild near Jordan, Minn. The 'Frontenac' parental variety was originally tested as MN 1047 and is described in *The Brooks and Olmo Register of New Fruit and Nut Varieties,* Third Edition, 1997, p. 265.

'Frontenac gris' originated as a single cane sport bearing gray colored fruit on a plant of the bluish black fruited 'Frontenac' variety growing at location Block 10 Row 16 Panel 7 at the HRC in 1992. When ripe, the berries of 'Frontenac gris' are gray and contain only slight amounts of anthocyanin pigment, whereas the 'Frontenac' parental variety produces highly pigmented dark bluish black berries. A total of 8 vines of 'Frontenac gris' were asexually propagated by hardwood cuttings from this original cane and planted at the HRC as follows: 2 plants were planted in 1995 in Block 10 Row 17 Panel 11; 3 plants were planted in 1996 in Block 18 Row 8 Panel 3; and 3 plants were planted in 1999 in Block 18 Row 11 Panel 5. These plants were observed through 2002, including their flowers and fruit, and were indistinguishable in appearance from the original 'Frontenac gris' cane. Therefore, the asexual progeny of 'Frontenac gris' are stable and reproduced true to type in successive generations.

The following data pertain to vines grown at the University of Minnesota Horticultural Research Center in Carver County, Minn. near Excelsior. For comparison purposes, data were collected for certain morphological descriptors from fruit of the variety 'Seyval', a grape variety commonly grown in Minnesota and the eastern United States for the production of white wine. Alphanumeric color designations refer to values based on the 1995 R.H.S. Colour Chart published by The Royal Horticultural Society, London, England. Many of the descriptors are based on those set forth by the International Board for Plant Genetic Resources in collaboration with the Office Internationale de la Vigne et du Vin (OIV) and the International Union for the Protection of New Varieties of Plants.

When dimensions, sizes, colors and other characteristics are given, it is to be understood that such characteristics are approximations set forth as accurately as possible. Variations of the usual magnitude incident to climatic factors, fertilization, pruning, pest control and other cultural practices are to be expected.

A) Mature Canes

The values presented are the means (with ranges in parentheses) of 10 canes observed from the 2002 growing season.

1. Color of canes: Striated, reddish brown. RHS colors 166A, 166C.
2. Internode length at base: 2.4 cm (2.1–3.0).
3. Internode length at midpoint: 9.3 cm (7.5–12.2).
4. Lenticels present: Yes (very small).
5. Lenticel color: 200A.
6. Cane cross-section shape: Elliptical.
7. Density of hairs on mature cane: None.
8. Tendril pattern on shoot: 2, 0, 2, 0 etc. (two nodes with a tendril followed by one node without).
9. Tendrils forked: Yes.
10. Tendril texture: Striated.
11. Tendril length: 15 cm (11–20).
12. Tendril color: 166C.
13. Bud width: 3.8 mm (3.1–5.0).
14. Bud shape: Triangular.
15. Bud color: 166B.

B) Trunk

The observations presented are from the 2002 growing season.

1. Bark texture: Somewhat flaky, small vertical segments approx. 1–2 cm.×4–6 cm.
2. Bark color: Silver-gray. RHS colors 201B, 201C.

C) Mature Leaves

Ten representative mature leaves from above the clusters in the middle third of the shoot were examined. The leaves were pressed and dried for later analysis. The values presented below are means (with ranges in parentheses) from collections in September 2000. Descriptors of mature leaves, including the designations N1 through N5, relate to "OIV—Code Numbers 065–093" of *Preliminary Minimal Descriptor List for Grapevine Varieties* (Dettweiler E., 1991, Instit üt fur Rebenzüchtung, Geilweilerhof, Germany).

| | | 'Frontenac gris' |
|---|---|---|
| 1. | Length of blade: | 15.3 cm (13.3–18.3) |
| 2. | Width of blade: | 15.5 cm (12.5–18.2) |
| 3. | Shape of blade: | circular-kidney shaped |
| 4. | Number of lobes: | 4.4 (3–5) |
| 5. | Length of vein N1: | 12.6 cm (10.5–15.0) |
| 6. | Length of vein N2: | 11.5 cm (9.7–13.5) |
| 7. | Length of vein N3: | 8.5 cm (7.3–9.3) |
| 8. | Length of vein N5: | 4.2 cm (2.9–5.5) |
| 9. | Length of N2 teeth: | 13.3 mm (10–16) |
| 10. | Width of N2 teeth: | 14.0 mm(11–16) |
| 11. | Length/width ratio of N2 teeth: | 0.96 (0.71–1.1) |
| 12. | Length of N4 teeth: | 8.2 mm (7–9) |
| 13. | Width of N4 teeth: | 11.9 mm (10–18) |
| 14. | Length/width ratio of N4 teeth: | 0.71 (0.5–0.9) |
| 15. | Shape of teeth: | rectilinear-convex |
| 16. | Shape of petiolar sinus: | wide open |
| 17. | Shape of base of petiolar sinus: | u-shaped |
| 18. | Depth of petiolar sinus: | 22.4 mm (17–29) |
| 19. | Width of petiolar sinus: | 48.6 mm (39–61) |
| 20. | Length of petioles: | 7.2 cm (4.7–9.6) |
| 21. | Shape of upper sinuses: | open |
| 22. | Shape of base of upper sinuses: | u-shaped |
| 23. | Pubescence on adaxial surface: | none |
| 24. | Pubescence on abaxial surface: | very sparse on main veins and at petiolar junction |
| 25. | Color of adaxial leaf surface: | 146B, yellow-green |
| 26. | Color of abaxial leaf surface: | 146C, yellow-green |
| 27. | Color of leaf Petiole | 59C, red-purple |

D) Young Shoots

The observations presented are from the 2002 growing season.

| | | 'Frontenac gris' |
|---|---|---|
| 1. | Form of shoot tip: | closed by small leaves |
| 2. | Density of prostate hairs on tip: | none |
| 3. | Density of erect hairs on tip: | very sparse |
| 4. | Petiole pigmentation: | dark red on adaxial, light red on abaxial |
| 5. | Shoot pigmentation: | adaxial striped to solid purple, abaxial striped |

E) Flowers

1. Fragrance: Moderately fragrant.
2. Mean time of flowering: June 14 when grown in Excelsior, Minn.
3. Color of petal: 145A, yellow-green.
4. Color of sepal: 144A, yellow-green.
5. Color of pollen: 4B, yellow.
6. Petal number: 5, fused in calyptra.
7. Petal shape: Cohering at summit and separating at base: 2.5 mm long; 1 mm wide at fused end; reflexed after dehiscence from flower.
8. Shape of cluster: Somewhat conical, typically with one shoulder.
9. Size of cluster: 14.5 cm long (range 10.1–19.8); 6.3 cm wide (range 3.6–11.1).
10. Number of flowers per cluster: 190 (range 111–278).
11. Size of individual entire flower: 5.6 mm long; 4.1 mm wide.
12. Pollen fertility: Yes, based on use in controlled pollinations.
13. Color of stamen: Anther: 162C, grayed-yellow. Filament: 155A, white.
14. Stamen number: 4.9 (range 4–6).
15. Pistil number: 1 per flower.
16. Pistil length: 2.5 mm.
17. Color of pistil: 144A, yellow-green.

F) Fruit

The values presented below are means (with ranges in parentheses) from fruit observed in the 2000 growing season, except for those traits indicated (**), which are means from the 2000–2003 growing seasons for 'Frontenac gris' and from the 1995 and 1999–2002 growing seasons for 'Seyval'.

| | 'Frontenac gris' | 'Seyval' |
|---|---|---|
| 1. Cluster length: | 17.4 cm (14.7–22.4) | 12.1 cm (9.0–15.1) |
| 2. Cluster weight** | 137.1 g (88–193) | 162.4 g (92–298) |
| 3. Cluster density: | loose-medium | medium |
| 4. Berry weight:** | 1.13 g (1.02–1.09) | 1.90 g (1.59–2.22) |
| 5. Berry length: | 11.4 mm (10.2–12.1) | 13.8 mm (12.2–15.4) |
| 6. Berry diameter at equator: | 11.3 mm (10.1–12.2) | 13.3 mm (12.1–15.3) |
| 7. Berry shape: | roundish | roundish |
| 8. Berry cross-section: | circular | circular |
| 9. Berry, color of skin: | gray-golden RHS color 151A Intermediate between 199C and 201C. | yellow-green |
| 10. Berry, color of flesh: | light green RHS colors 160A, 160B | light green RHS color 150D |
| 11. Berry, particular flavor: | lightly fruity (peach, kiwi) | neutral |
| 12. Length of pedicel: | 5.7 mm | 6.2 mm |
| 13. Berry, separation from pedicel: | difficult | difficult |
| 14. Berry, presence of seeds: | fully developed | fully developed |
| 15. Seed number/berry: | 2.4 (2–4) | 2.2 (1–4) |
| 16. Seed length: | 0.53 mm (0.50–0.55) | 0.59 mm (0.54–0.65) |
| 17 Seed width: | 0.33 mm (0.31–0.36) | 0.39 mm (0.35–0.46) |
| 18. Seed length/width ratio: | 1.61 | 1.51 |
| 19. Seed weight: | 0.023 g | 0.031 g |
| 20. Seed color: | RHS color 165A | RHS color 177A |

G) Harvest Parameters

Values represent the means (with ranges in parentheses) for fruit harvested over four growing seasons (1999–2003) for 'Frontenac gris' and six growing seasons (1995, 1996, 1999–2002) for 'Seyval'.

| | 'Frontenac gris' | 'Seyval' |
|---|---|---|
| 1. Harvest date: | 9/29 (9/18–10/5) | 9/26 (9/16–10/6) |
| 2. Brix: | 26.30° (24.6°–26.8°) | 20.9°(18.6°–23.2°) |
| 3. pH: | 3.06 (2.85–3.18) | 3.11 (2.91–3.41) |
| 4. % titratable acidity: | 1.22% (1.06–1.41%) | 0.86% (0.72–1.02%) |

H) Vineyard Performance

Based on observations compiled over four years (1999–2003).

1. Susceptibility to powdery mildew (*Uncinula necator*): Moderate.
2. Susceptibility to downy mildew (*Plasmopara viticola*): Very low.
3. Susceptibility to black rot (*Guignardia bidwellii*): Low-moderate.
4. Susceptibility to bunch rot (*Botrytis,* etc): Very low.
5. Susceptibility to foliar phylloxera (*Daktulosphaira vitifoliae*): Moderate-severe.
6. Susceptibility to crown gall (*Agrobacterium tumefaciens*): No natural infection observed.
7. Susceptibility to phenoxy herbicide drift (e.g., 2,4-D): Low.
8. Berry splitting: Low.
9. Berry shelling: Low.
10. Vigor level: High.
11. Winter hardiness: High, trunks have survived −38° C.
12. Wood ripening: Very good.

I) Wine Quality

Descriptions below are compiled from observations on wine made from 'Frontenac gris' fruit harvested during the 1999–2003 growing seasons.

1. Flavors and aromas: Peach, apricot, citrus, tropical fruit; no 'hybrid', herbaceous, or labrusca aromas.
2. Balance: Good body, well balanced when finished with residual sugar or put through malolactic fermentation.
3. Color: Attractive light pink/peach unless filtered or fined.
4. Propensity for oxidation: Low.
5. Overall quality: Very good.

What is claimed is:

1. A new and distinct variety of grape plant designated 'Frontenac gris' as described and illustrated herein.

* * * * *

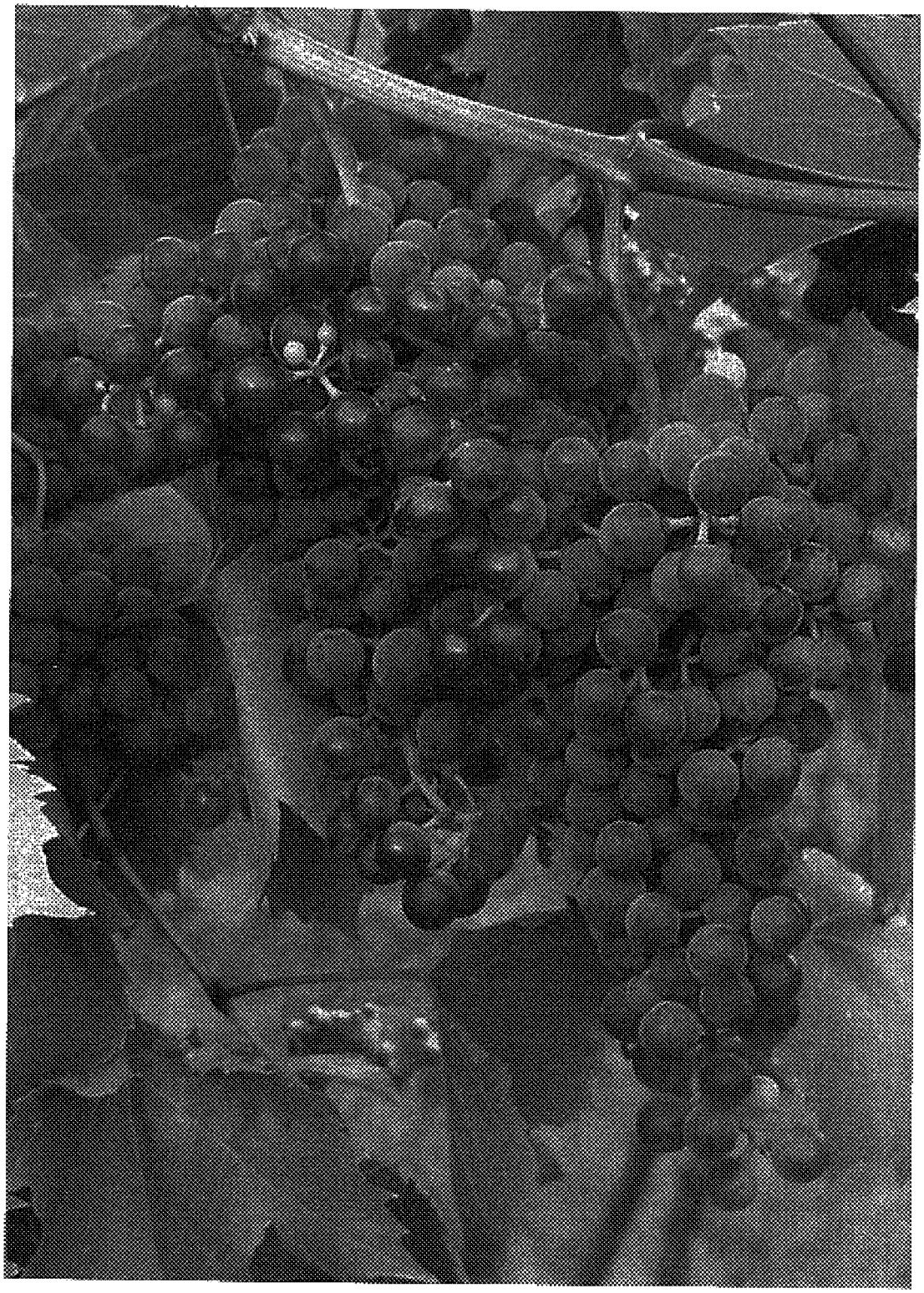
Figure One

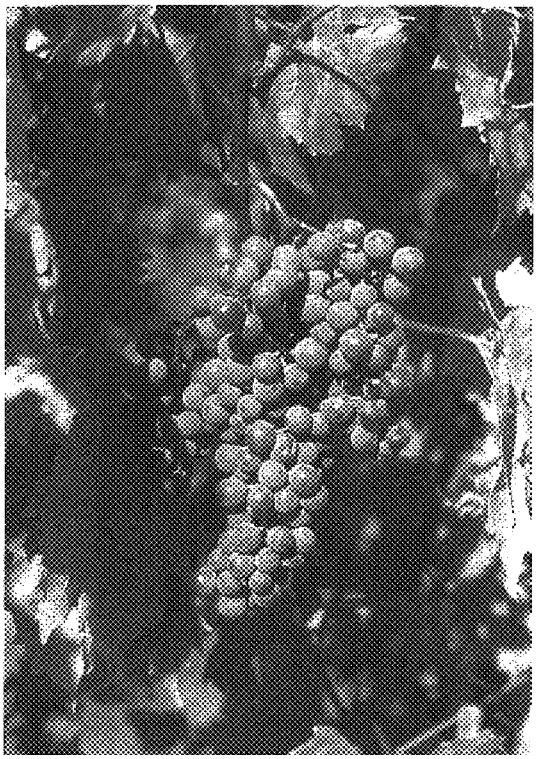
Figure Two
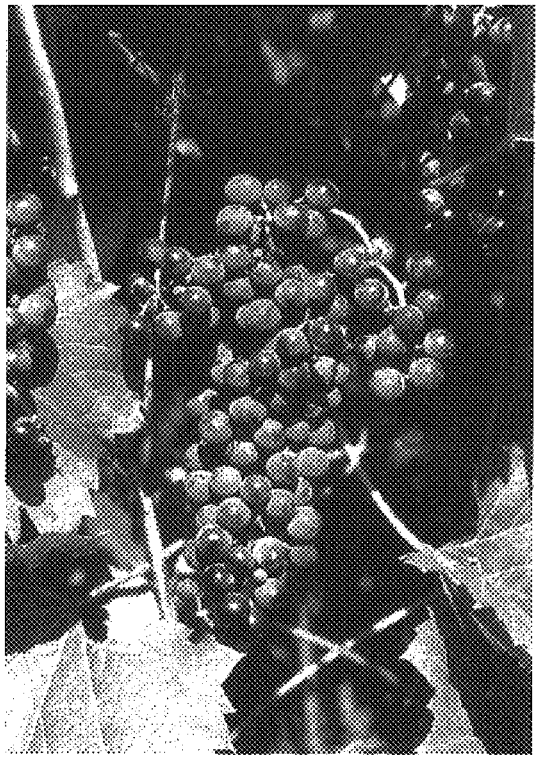
Figure Three

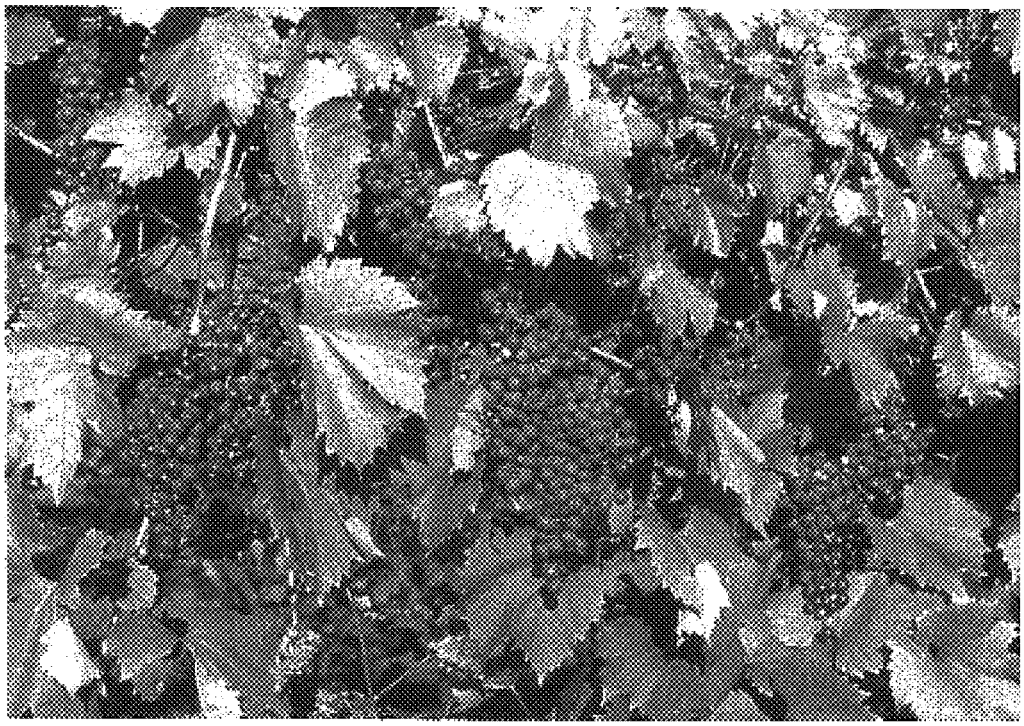
Figure Four
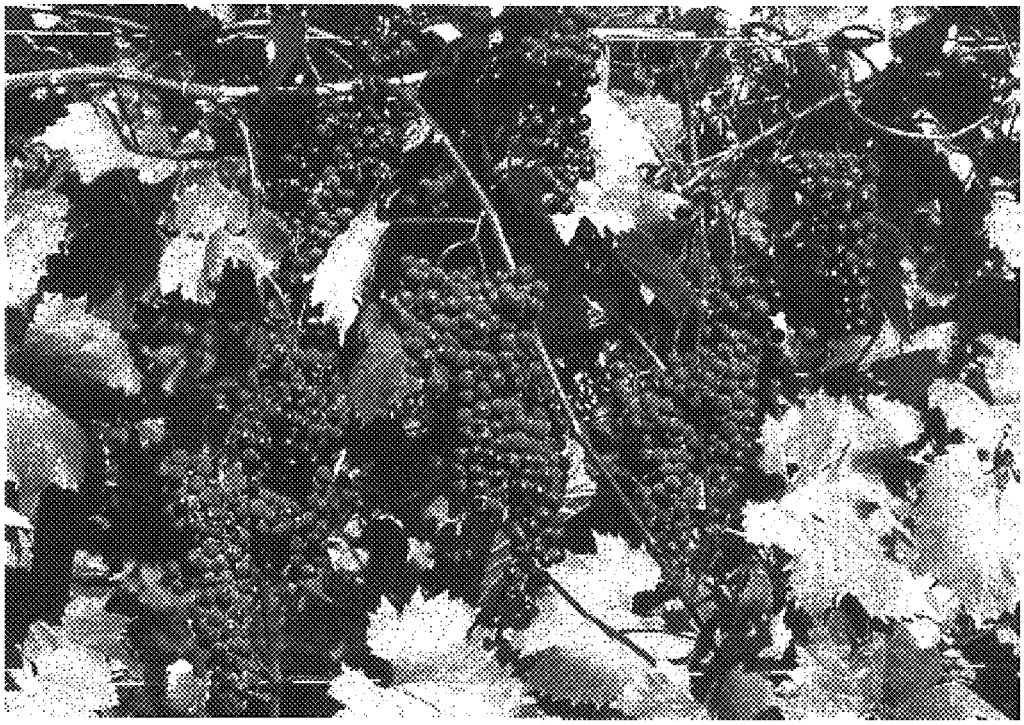
Figure Five

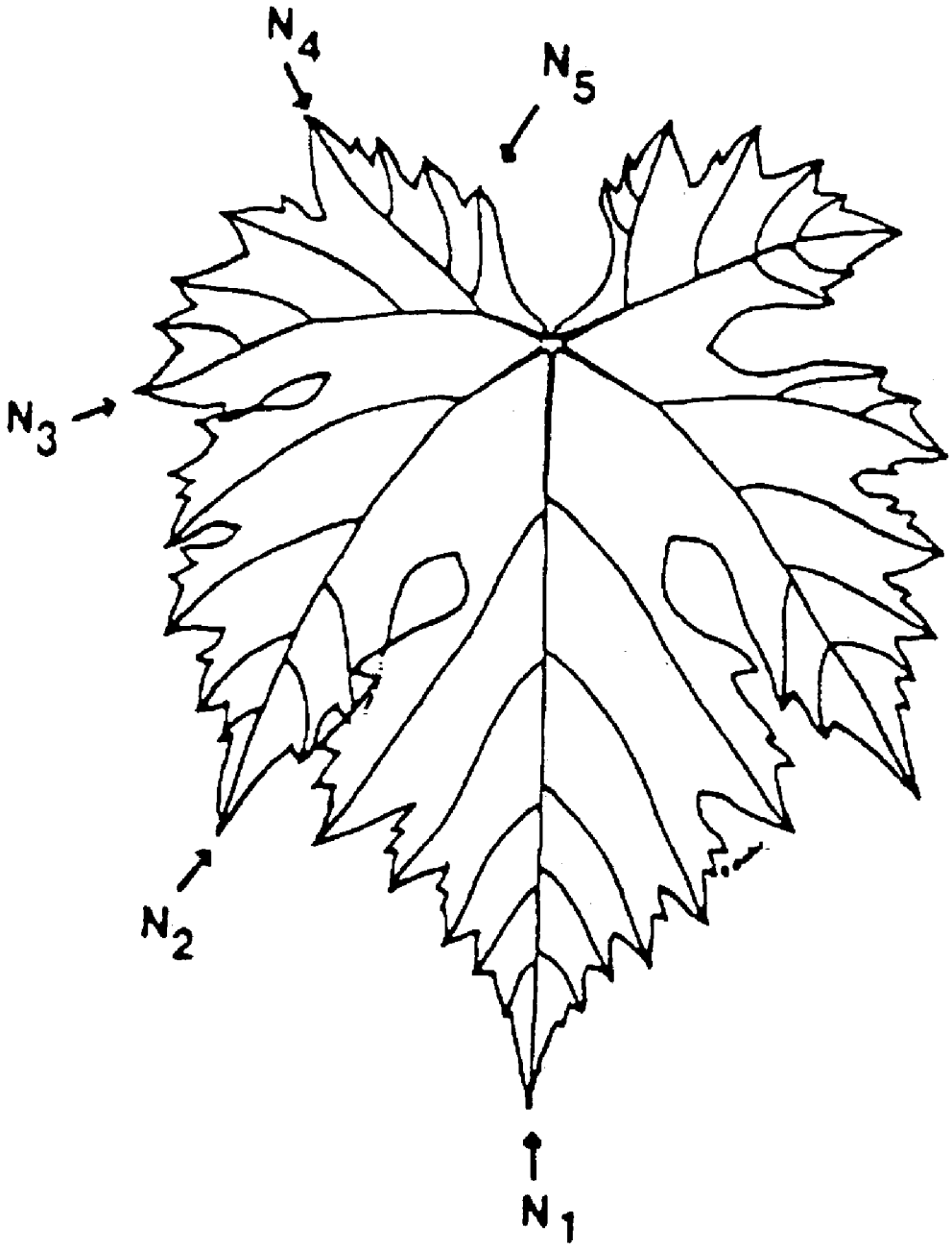
Figure Six